United States Patent [19]

Lyssy

[11] 4,047,422
[45] Sept. 13, 1977

[54] PROCESS FOR MEASURING PERMEABILITY TO GAS OF WALLS AND/OR CLOSURE OF THREE-DIMENSIONAL ENCASING ELEMENTS

[76] Inventor: Georges H. Lyssy, Rotfluhstrasse 87, CH 8702 Zollikon, Zurich, Switzerland

[21] Appl. No.: 677,849

[22] Filed: Apr. 16, 1976

[30] Foreign Application Priority Data

Apr. 18, 1975 Switzerland ............... 004969/75

[51] Int. Cl.² .................. G01N 15/08; G01M 3/34
[52] U.S. Cl. ............................. 73/38; 73/49.3
[58] Field of Search ............ 73/38, 40, 49.2, 49.3

[56] References Cited

U.S. PATENT DOCUMENTS

| | | | |
|---|---|---|---|
| 3,060,724 | 10/1962 | Smith, Jr. et al. | 73/38 X |
| 3,352,146 | 11/1967 | Lyssy | 73/38 |
| 3,813,923 | 6/1974 | Pendleton | 73/49.2 |

Primary Examiner—Richard C. Queisser
Assistant Examiner—Charles Gorenstein
Attorney, Agent, or Firm—Wenderoth, Lind & Ponack

[57] ABSTRACT

A filled or gas encasing element to be tested is placed in a measuring chamber. The free space between the element and the chamber is filled with filler elements to prevent bursting or inflation of the element. A vacuum is produced in the chamber, and the time required to achieve a predetermined pressure increase therein is measured.

3 Claims, 1 Drawing Figure

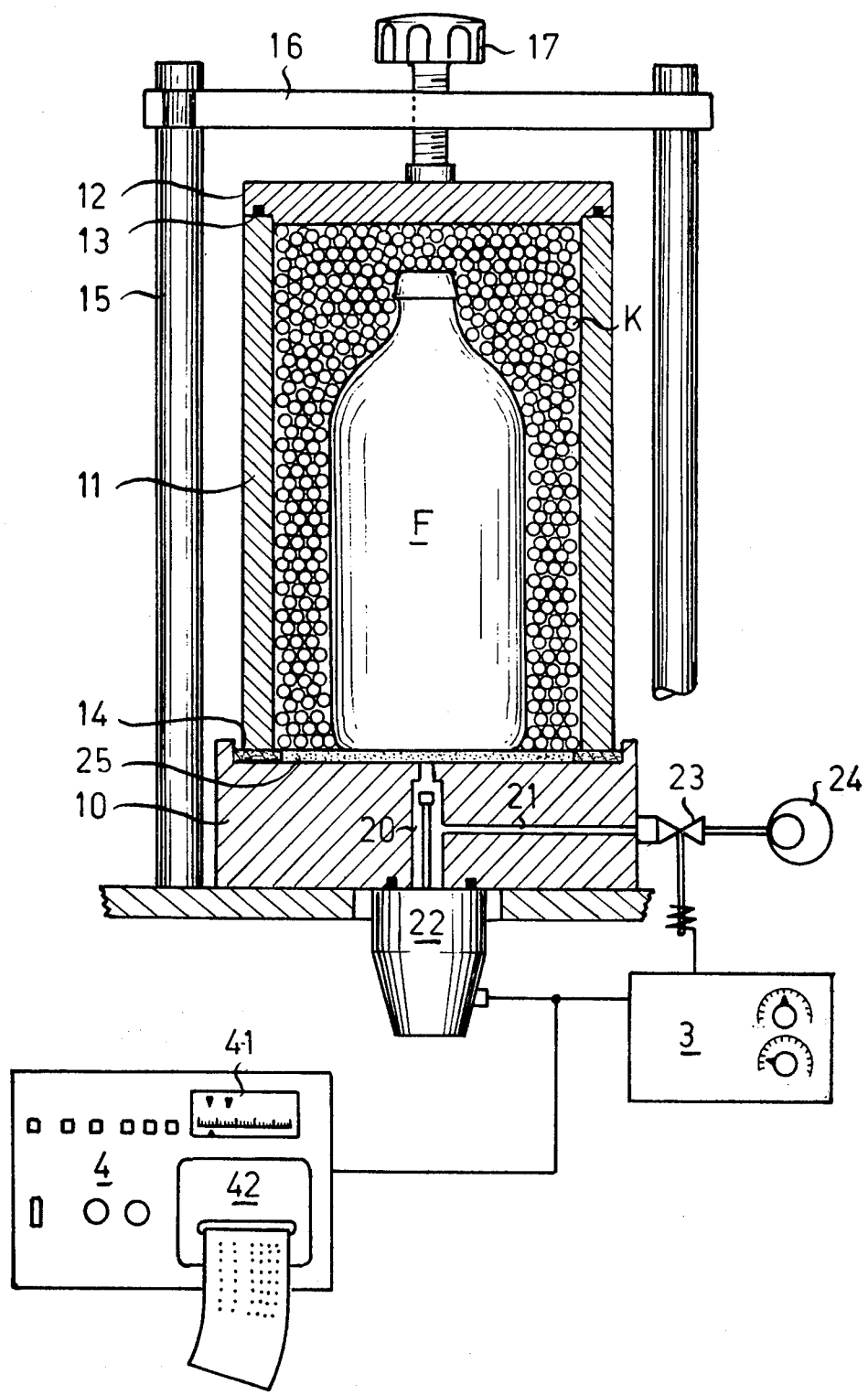

PROCESS FOR MEASURING PERMEABILITY TO GAS OF WALLS AND/OR CLOSURE OF THREE-DIMENSIONAL ENCASING ELEMENTS

BACKGROUND OF THE INVENTION

The present invention relates to a process for measuring the permeability to gas of the walls and/or the closure of threedimensional encasing elements, such as heat-sealed packages, bottles or cans, in accordance with a manometric measuring method.

Under the manometric measuring method for determining the permeability of an encasing element for gas, vacuum is produced on the outer side of the test piece. In accordance with the permeability of the encasing element a certain amount of gas passes through the wall per unit of time and brings about an increase in pressure. The permeability to gas can be calculated from the increase in pressure per unit of time.

In regard to the testing of sheets, standards are available for the calculation, e.g., in accordance with the DIN No. 53380. According to this standard, the permeability to gas is expressed in $cm^3$ of diffused amount of gas per 24 hours and per $m^2$ of sheet surface. The amount of gas is converted in this connection to the volume at 0° C and 760 torr.

The measuring method worked out for sheets can logically be transferred to closed encasing elements. However, the degree of permeability determined in this connection can be expressed only as an amount per test piece.

Of course, this process which is already novel as such could be realized only on encasing elements that are able to bear a pressure difference of one atmosphere, such as relatively thick-walled bottles. On the other hand, the manometric measuring method cannot be readily applied to thin-walled or semirigid encasing elements, such as bottles of synthetic resin or soft foil packs, since the encasing element is inflated or bursts apart during the measurement.

SUMMARY OF THE INVENTION

The object of the present invention is to provide a method for measuring permeability to gas, whereby it is possible to test thin-walled or semirigid encasing elements. This object is achieved according to the invention by providing a process characterized in that the filled or gas encasing element to be tested is placed into a measuring chamber and the free space between the encasing element and the inner wall of the measuring chamber is filled with filler elements that protect the encasing element against bursting or inflation, a vacuum is produced in the measuring chamber and the time is measured within which a certain pressure-increase interval is traversed, the time representing a criterion for the leakage rate of the encasing element and/or its closure.

To ensure the reliability of the result of measurement it is of advantage to repeat the measurement a number of times, the evacuation being repeated each time after the selected pressure-increase interval is traversed. This can be realized with an apparatus including a three-part vacuum-type measuring chamber, that is a firm lower part which is provided with a vacuum cock and a vacuum measuring element, and an intermediate element with a cover which can be placed on such lower part in a vacuum tight manner, the intermediate element being adapted in size to the test piece.

BRIEF DESCRIPTION OF THE DRAWING

The drawing schematically illustrates an exemplified embodiment of an apparatus for carrying out the process of the invention.

DETAILED DESCRIPTION OF THE INVENTION

The apparatus comprises a three-part measuring chamber including a firm lower part 10, on which there is placed a cylindrical part 11 with a cover 12. These parts are sealed in a vacumm tight manner in relation to each other. A packing ring 13 is employed for sealing the cover and a packing ring 14 is employed for sealing lower part 10. In addition, the three parts are pressed together with a screw 17 by means of pull rods 15 and a traverse 16.

Bores 20, 21 are arranged in lower part 10. The probe of a Pirani vacuum measuring element 22 projects into bore 20, while a vacuum pump 24 is connected to bore 21 through an electrically operated valve 23. A porous sintered metal disk 25, surrounded by packing ring 14, rests on lower part 10.

A signal amplifier 3 and an electronic measuring device 4 comprising a vacuum indicator 41 and a printer 42 are connected to the Pirani measuring element.

The permeability to gas of an empty bottle F of synthetic resin may be tested. This is a bottle that should be used for the transportation of beer. The permeability for carbon dioxide ($CO_2$) is of importance in this connection. Accordingly, the bottle is first filled (gassed) with $CO_2$ under atmospheric pressure and then closed in a proper manner. Subsequently, the bottle is placed into the measuring chamber and the cavity remaining around the bottle is filled with steel pellets K. The measuring chamber is then closed and evacuation is effected by means of pump 24, e.g., to 0.02 torr. On the basis of the signal from measuring device 4, the signal amplifier closes valve 23. The time interval required by the carbon dioxide escaping through the wall of the bottle to effect a pressure increase from 0.03 to 0.06 torr is measured. Such a time is recorded by printer 42 on a strip of paper. Then the evacuation is performed again to 0.02 torr and the measurement is repeated. The steps are effected automatically. Measuring device 4 is provided for this purpose with contact makers that control the signal amplifier.

The measuring method described above produces comparative values. In order to obtain absolute values, one must know the volume which remains around bottle F in the measuring chamber and which is to be evacuated. The volume can be calculated from the following equation:

$$V_M - V_F - V_K = V_E,$$

wherein:
$V_M$ = volume of the measuring chamber,
$V_F$ = volume of the bottle,
$V_K$ = volume of the pellets,
$V_E$ = volume to be evacuated.

$V_M$ is known from the construction. The volume of the measuring chamber together with adjacent bores 20, 21 will be selected such that it simplifies the calculation, i.e., in accordance with the size of cylinder 11, e.g., 1000 $cm^3$ or 600 $cm^3$.

The volume of bottle F can be readily determined and the volume of the pellets can be determined in various ways.

Volume $V_K$ of the pellets can be determined by weighing the pellets and on the basis of the specific gravity of the material (steel) from which the pellets are made.

A calculation which is less precise but sufficient for most cases proceeds from the assumption that the pellets occupy an ideal packed state, which makes out about 60% of the volume, so that $V_K \approx 0.6(V_M - V_F)$, hence $$V_E \approx 0.4(V_M - V_F).$$

Finally, it is also possible to determine manometrically the volume of the pellets or of the space to be evacuated, by evacuating the measuring chamber to a certain value, then introducing a known amount of air by means of a calibrated cock plug and then measuring the increase in pressure. Volume $V_E$, which is to be evacuated and which is of importance, can then be calculated from $$V_H P_L + V_M P_M = V_E P_{tot}$$

wherein:

$V_H$ = volume of the cock plug,
$P_L$ = pressure of the air introduced from the environment,
$V_M$ = volume of the measuring chamber,
$P_M$ = pressure in the measuring chamber prior to the introduction of air,
$V_E$ = volume to be evacuated,
$P_{tot}$ = pressure in the measuring chamber after the introduction of air.

Since every pressure and volume except $V_E$ is known, $V_E$ can be calculated.

After $V_E$ is determined in accordance with one of the above-mentioned methods, absolute values of permeability to gas of the encasing element and/or its closure can be calculated from the measured results in units of cm$^3$ per 24 hours under normal conditions.

It is indeed of advantage to use steel pellets for filling up the cavity, since the pellets can then be removed from the measuring chamber by means of a magnet. However, one can readily use other filler elements, such as pebbles, glass spheres or the like for filling up the cavity. Specially shaped fillers, the so-called "FAST FLOW" or "FREE FLOW" (trademark designations) elements, can also be used.

In the example described above, the permeability of the wall of bottle F is determined for $CO_2$. However, the measuring method of the invention is suitable for measuring the permeability to gas of filled encasing elements, e.g., bottles filled with beer or cans filled with coffee as well as of so-called soft packages, i.e., goods that are packed between heat-sealed foils, such as slices of ham or cheese. The measurement then produces permeability values for the air included in the encasing element or the protective gas or gas mixture that is included. The term "closure" in such case refers to the weld seam of the wrapping foil.

In the latter case, wherein the permeability to gas of flat soft packages is to be tested, it is of advantage to use a measuring chamber of rectangular cross section in place of a cylindrical measuring chamber.

I claim:

1. A process for measuring the permeability to gas of the walls and/or the closure of three-dimensional encasing elements, such as packages, bottles or cans, in accordance with a manometric measuring method, said process comprising:

placing a filled or gas encasing element which is to be tested into a measuring chamber;
filling the free space between said encasing element and the inner wall of said measuring chamber with filler elements that protect the encasing element against bursting or inflation;
producing a vacuum in said measuring chamber; and
measuring the time within which a certain pressure increase within said measuring chamber occurs, such time representing a criterion for the leakage rate of the encasing element and/or its closure.

2. A process as claimed in claim 1, wherein said measuring chamber comprises a known volume from which the volume of said encasing element and that of said filler elements are subtracted, in order to be able to calculate therefrom an absolute value of the quantity of gas diffused per unit of time.

3. A process as claimed in claim 1, wherein the measurement is repeated a plurality of times, the evacuation being repeated each time after the selected pressure increase occurs.

* * * * *